US010689560B2

(12) United States Patent
Al-Yami et al.

(10) Patent No.: US 10,689,560 B2
(45) Date of Patent: *Jun. 23, 2020

(54) FLEXIBLE DURABLE CEMENT

(71) Applicant: Saudi Arabian Oil Company, Dhahran (SA)

(72) Inventors: Abdullah Al-Yami, Dhahran (SA); Vikrant Wagle, Abqaiq (SA); Hussain Albahrani, Qatif (SA); Zainab Alsaihati, Saihat (SA); Antonio Santagati, Dhahran (SA); Mohammad Al-Alqam, Dhahran (SA); Ali Alsafran, Dhahran (SA); Abdulaziz Alhelal, Alhsa Hofuf (SA); Nasser Alhareth, Ras Tanura (SA); Abdullah Al-Awadh, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/265,358

(22) Filed: Feb. 1, 2019

(65) Prior Publication Data

US 2019/0284465 A1 Sep. 19, 2019

Related U.S. Application Data

(63) Continuation of application No. 15/924,942, filed on Mar. 19, 2018.

(51) Int. Cl.
*E21B 33/13* (2006.01)
*C09K 8/44* (2006.01)
*C07C 39/06* (2006.01)
*C08L 33/20* (2006.01)
*C04B 38/02* (2006.01)
*C09K 8/46* (2006.01)
*C04B 28/04* (2006.01)
*C09K 8/467* (2006.01)

(52) U.S. Cl.
CPC ............... *C09K 8/44* (2013.01); *C04B 28/04* (2013.01); *C04B 38/02* (2013.01); *C07C 39/06* (2013.01); *C08L 33/20* (2013.01); *C09K 8/46* (2013.01); *C09K 8/467* (2013.01); *E21B 33/13* (2013.01)

(58) Field of Classification Search
CPC . C09K 8/44; C07C 39/06; C08L 33/20; E21B 33/13
See application file for complete search history.

(56) References Cited

U.S. PATENT DOCUMENTS

| | | | |
|---|---|---|---|
| 3,635,289 A | 1/1972 | Van Dyk | |
| 4,430,465 A | 2/1984 | Abbott | |
| 5,147,459 A | 9/1992 | Lynn et al. | |
| 5,330,827 A * | 7/1994 | Hansen | C04B 16/0625 428/294.7 |
| 6,582,819 B2 * | 6/2003 | McDaniel | A63K 1/00 166/295 |
| 6,626,243 B1 | 9/2003 | Go Boncan | |
| 2006/0283595 A1 | 12/2006 | Santra et al. | |
| 2008/0200354 A1 | 8/2008 | Jones et al. | |
| 2009/0250219 A1 | 10/2009 | Debruijn et al. | |
| 2011/0308799 A1 | 12/2011 | Tarafdar et al. | |
| 2012/0015852 A1 | 1/2012 | Quintero et al. | |
| 2014/0110119 A1 | 4/2014 | Luyster et al. | |
| 2014/0274815 A1 * | 9/2014 | Lovett | C04B 16/0625 507/118 |
| 2014/0318785 A1 | 10/2014 | Reddy et al. | |
| 2014/0364535 A1 * | 12/2014 | Chatterji | C04B 28/02 523/130 |
| 2014/0374099 A1 | 12/2014 | Wagle et al. | |
| 2016/0130496 A1 * | 5/2016 | Holtsclaw | C04B 24/32 507/226 |
| 2016/0244613 A1 * | 8/2016 | Nazar | C08L 95/005 |
| 2016/0244655 A1 | 8/2016 | Reddy et al. | |
| 2017/0015775 A1 | 1/2017 | Holmberg et al. | |

FOREIGN PATENT DOCUMENTS

| | | |
|---|---|---|
| CA | 2322937 A1 | 4/2001 |
| CA | 2541274 C | 1/2012 |
| CA | 2832791 A1 | 5/2015 |
| EP | 2457974 A1 | 5/2012 |
| EP | 2615151 A1 | 7/2013 |
| WO | 9200251 A1 | 1/1992 |
| WO | 0037387 A1 | 6/2000 |
| WO | 02062719 A2 | 8/2002 |
| WO | 2007031736 A1 | 3/2007 |
| WO | 2009093006 A1 | 7/2009 |
| WO | 2012022399 A1 | 2/2012 |
| WO | 2014036545 A1 | 3/2014 |
| WO | 2015034478 A1 | 3/2015 |
| WO | 2016053237 A1 | 4/2016 |

OTHER PUBLICATIONS

Office Action dated Feb. 14, 2019 pertaining to U.S. Appl. No. 15/924,942, filed Mar. 19, 2018, 32 pgs.
U.S. Office Action dated Jun. 4, 2019 pertaining to U.S. Appl. No. 15/924,942, filed Mar. 19, 2018, 17 pgs.
U.S. Office Action dated Jun. 20, 2019 pertaining to U.S. Appl. No. 15/964,420, filed Apr. 27, 2018, 37 pgs.
Office Action dated Sep. 10, 2019 pertaining to U.S. Appl. No. 15/924,942, filed Mar. 19, 2018, 16 pgs.
Office Action dated Nov. 8, 2019 pertaining to U.S. Appl. No. 16/582,467, filed Sep. 25, 2019, 19 pgs.
Final Office Action dated Nov. 8, 2019 pertaining to U.S. Appl. No. 15/964,420, filed Apr. 27, 2018, 13 pgs.

(Continued)

*Primary Examiner* — Silvana C Runyan
(74) *Attorney, Agent, or Firm* — Dinsmore & Shohl LLP

(57) ABSTRACT

According to at least one embodiment of the present description, a cement slurry includes 50% to 90% BWOC of a cement precursor material based on a total weight of the cement slurry; and from 10% to 50% BWOC of a flexible additive based on the total weight of the cement slurry. The flexible additive includes hydrophilic polyolefin fibers or 2,6-di-tert-butyl-p-cresol.

11 Claims, No Drawings

(56) References Cited

OTHER PUBLICATIONS

Examination Report dated Jan. 7, 2020 pertaining to GCC Application Serial No. 2018-36007 filed Sep. 16, 2018.
Office Action dated Dec. 31, 2019 pertaining to U.S. Appl. No. 15/924,942, filed Mar. 19, 2018, 12 pgs.
Notice of Allowance dated Jan. 23, 2020 pertaining to U.S. Appl. No. 15/964,420, filed Apr. 27, 2018, 5 pgs.
Notice of Allowance dated Jan. 30, 2020 pertaining to U.S. Appl. No. 116/582,467, filed Sep. 25, 2019, 9 pgs.

* cited by examiner

FLEXIBLE DURABLE CEMENT

CROSS REFERENCE TO RELATED APPLICATIONS

This application is a continuation application of U.S. patent application Ser. No. 15/924,942 filed Mar. 19, 2018, the entire disclosure of which is hereby incorporated herein by reference.

TECHNICAL FIELD

Embodiments of the present description generally relate to natural resource well drilling and, more specifically, to flexible durable cements utilized in well drilling processes.

BACKGROUND

In well drilling processes, wellbores are commonly cemented, where the annulus between the casing and the wellbore wall is filled with cement, forming a cement sheath. High internal pressure may expand the casing and the cement sheath, which causes tensile stress on the cement sheath. Generally, cement materials are brittle, and the compressive strength is greater than the tensile strength of cement formations. Accordingly, the increased tensile stress on the cement sheath caused by the internal pressure may cause damage, such as cracking or fracture, to the cement sheath, which may lead to undesired leaking.

The damage to the cement sheath described in the preceding paragraph may be worsened by the high density of cement materials commonly used as cement sheaths in wellbores. Specifically, greater density cement materials are used in wellbores because they have less voids in the cement structures, which results in less migration of hydrocarbons from the geological formation into the well. However, the low number of voids in the cement material can increase the brittleness of the cement material, which may lead to damage of the cement structure when pressure is applied to the cement structure.

SUMMARY

Accordingly, there is a need for flexible additives that can be added to cement slurries to increase the flexibility of the cement materials used in wellbores. Particularly, there is a need for flexible additives that allow the cement material to shift when exposed to tensile stress without damaging the cement structure, particularly after or during exposure of the cement to high internal pressure environments. As referred to in this application, high internal pressure is pressure generated from fracturing operations. In fracturing operations, high pressure is created by injecting fluid into a well to break geological formations. This pressure can also cause damage to well cement.

The present flexible additives improve damage resistance to the cement structures in which they are included by providing a flexible polymeric structure in the cement structure, which decreases the Young's modulus and increases the Poisson's ratio of the cement. Conventional cement additives are not able to provide the Young's modulus and Poisson's ratio achieved by the present flexible additives.

The presently described flexible additives are generally comprised of one or more hydrophilic polyolefin fiber. In one or more embodiments, the flexible additive may be comprised of 2,6-di-tert-butyl-p-cresol. The flexible additive may be added to the cement slurry in various amounts depending on the properties of the wellbore and the composition and properties of the cement material. For instance, a greater concentration of the flexible additive may be added to cement materials that have greater density and a lesser concentration of the flexible additive may be added to cement materials that have a lesser density. The presently disclosed flexible additive may be added to the cement material as a dry ingredient to the dry cement mixture, or the flexible additive may be added to the cement slurry.

In one embodiment, a cement slurry comprises 50% to 90% BWOC of a cement precursor material based on a total weight of the cement slurry; and from 10% to 50% BWOC of a flexible additive based on the total weight of the cement slurry. The flexible additive comprises hydrophilic polyolefin fibers or 2,6-di-tert-butyl-p-cresol. In some embodiments, the flexible additive consists or consists essentially of 2,6-di-tert-butyl-p-cresol.

In another embodiment, a wellbore cementing system comprises: a tubular positioned in a wellbore such that an annulus is formed between a geological formation and the tubular; and a cement structure positioned in at least a portion of the annulus. The cement structure comprises from 10% to 50% by weight of the cement (BWOC) of a flexible additive, and the flexible additive comprises hydrophilic polyolefin fibers or 2,6-di-tert-butyl-p-cresol. In some embodiments, the flexible additive consists or consists essentially of 2,6-di-tert-butyl-p-cresol.

Additional features and advantages of the described embodiments will be set forth in the detailed description which follows, and in part will be readily apparent to those skilled in the art from that description or recognized by practicing the described embodiments, including the detailed description which follows as well as the claims.

DETAILED DESCRIPTION

In the present description, the following terms or units of measurement have been abbreviated, where:
° F.=degrees Fahrenheit;
OBM=oil-based mud;
kg/m$^3$=kilogram per cubic meter;
g/cc=grams per cubic centimeter;
BWOC=by weight of the cement;
gps=gallons per sack;
LVTD=linear variable differential transformer
psi=pounds per square inch;
rpm=rotations per minute; and
pcf=pound per cubic foot.

Embodiments of the present description are directed to flexible additives to be added to cement materials, such as cement slurries, and methods of using flexible additives in cement slurries that result in a cement having, among other attributes, improved tensile strength as measured by the Young's modulus and Poisson's ratio of the cement. As used throughout the description, "flexible additive" refers to a component or mixture of components that are present in the cement material or cement slurry and, when the cement has hardened into a cement structure, adds flexibility to the cement structure. A "cement slurry" refers to a slurry which is cured to form a cement. In some embodiments, a cement slurry comprises 50% to 90% BWOC of a cement precursor material based on a total weight of the cement slurry; and from 10% to 50% BWOC of a flexible additive based on the total weight of the cement slurry. The flexible additive comprises hydrophilic polyolefin fibers or 2,6-di-tert-butyl-p-cresol. In another embodiment, a wellbore cementing system comprises: a tubular positioned in a wellbore such that an annulus is formed between a geological formation and the tubular; and a cement structure positioned in at least a portion of the annulus. The cement structure comprises from 10% to 50% BWOC of a flexible additive, and the flexible additive comprises hydrophilic polyolefin fibers or 2,6-di-tert-butyl-p-cresol. In some embodiments, the flexible additive consists or consists essentially of 2,6-di-tert-butyl-p-cresol.

A wellbore is a hole that extends from the surface to a location below the surface. The wellbore can permit access as a pathway between the surface and a hydrocarbon-bearing formation. The wellbore, defined and bound along its operative length by a wellbore wall, extends from a proximate end at the surface, through the subsurface, and into the hydrocarbon-bearing formation, where it terminates at a distal wellbore face. The wellbore forms a pathway capable of permitting both fluid and apparatus to traverse between the surface and the hydrocarbon-bearing formation.

Besides defining the void volume of the wellbore, the wellbore wall also acts as the interface through which fluid can transition between the interior of the wellbore and the formations through which the wellbore traverses. The wellbore wall can be unlined (that is, bare rock or formation) to permit such interaction with the formation or lined (that is, with casing, tubing, production liner or cement) so as to not permit such interactions.

The wellbore usually contains at least a portion of at least one tubular (that is, a fluid conduit) that links the interior of the wellbore to the surface. Examples of such fluid conduits or tubulars include casing, liners, pipes, tubes, coiled tubing and mechanical structures with interior voids. A fluid conduit connected to the surface is capable of permitting regulated fluid flow and access between equipment on the surface and the interior of the wellbore. Example equipment connected at the surface to the fluid conduit includes pipelines, tanks, pumps, compressors and flares. The fluid conduit is sometimes large enough to permit introduction and removal of mechanical devices, including tools, drill strings, sensors and instruments, into and out of the interior of the wellbore.

The fluid conduit made from a tubular usually has at least two openings (typically on opposing ends) with an enclosing surface having an interior and exterior surface. The interior surface acts to define the bounds of the fluid conduit. Examples of tubulars and portions of tubulars used in the wellbore as fluid conduits or for making or extending fluid conduits include casing, production liners, coiled tubing, pipe segments and pipe strings. An assembly of several smaller tubulars connected to one another, such as joined pipe segments or casing, can form a tubular that acts as a fluid conduit.

When positioning a tubular or a portion of tubular in the wellbore, the volume between the exterior surfaces of the fluid conduit or tubular portion and the wellbore wall of the wellbore forms and defines a wellbore annulus. The wellbore annulus has a volume in between the external surface of the tubular or fluid conduit and the wellbore wall.

The wellbore contains wellbore fluid from the first moment of formation until completion and production. The wellbore fluid serves several purposes, including well control (hydraulic pressure against the fluids in the hydrocarbon-bearing formation), wellbore wall integrity (hydraulic pressure on the wellbore wall; provides loss control additives) and lubricity (operating machinery). Wellbore fluid is in fluid contact with all portions of the wellbore and everything in the wellbore that is not fluidly isolated, including the tubular internal fluid conduit, the wellbore annulus, and the wellbore wall. Other fluid conduits coupled to the wellbore often contain at least some wellbore fluid.

While drilling, drilling fluid ("mud") fills the interior of the wellbore as the wellbore fluid. Some muds are petroleum-based materials and some are water-based materials. Petroleum-based materials comprise at least 90 weight percent of an oil-based mud (OBM). Examples of suitable base petroleum materials include crude oils, distilled fractions of crude oil, including diesel oil, kerosene and mineral oil, and heavy petroleum refinery liquid residues. A minor part of the OBM is typically water or an aqueous solution that resides internally in the continuous petroleum phase. Other OBM components can include emulsifiers, wetting agents and other additives that give desirable physical properties.

While performing drilling operations, wellbore fluid circulates between the geological surface and the wellbore interior through fluid conduits. Wellbore fluid also circulates around the interior of the wellbore. The introduction of drilling fluid into the wellbore through a first fluid conduit at pressure induces the motivation for the fluid flow in the wellbore fluid. Displacing wellbore fluid through a second fluid conduit connected to the surface causes wellbore fluid circulation from the first fluid conduit to the second fluid conduit in the interior of the wellbore. The expected amount of wellbore fluid displaced and returned to the surface through the second fluid conduit is equivalent to the amount introduced into the wellbore through the first fluid conduit. Parts of the wellbore that are fluidly isolated do not support circulation.

The circulation and differences in movement of wellbore fluid within the wellbore can cause internal pressure of the wellbore to increase. This increase in internal pressure can place stresses on the components of the wellbore, such as, for example, the tubular. Therefore, a cement structure can be placed between the geological formation and the tubular.

Cementing is one of the most important operations in both drilling and completion of the wellbore. Primary cementing occurs at least once to secure a portion of the fluid conduit between the wellbore interior and the surface to the wellbore wall of the wellbore.

Primary cementing forms a protective solid sheath around the exterior surface of the introduced fluid conduit by positioning cement slurry in the wellbore annulus. Upon positioning the fluid conduit in a desirable location in the wellbore, introducing cement slurry into the wellbore fills at least a portion, if not all, of the wellbore annulus. When the cement slurry cures, the cement physically and chemically bonds with both the exterior surface of the fluid conduit and the wellbore wall, such as a geological formation, coupling the two. In addition, the solid cement provides a physical barrier that prohibits gases and liquids from migrating from one side of the solid cement to the other via the wellbore annulus. This fluid isolation does not permit fluid migration uphole of the solid cement through the wellbore annulus.

Displacing wellbore fluid for primary cementing operations is similar to establishing circulation in the wellbore fluid with a drilling mud. An amount of cement slurry introduced into the wellbore through a first fluid conduit induces fluid flow in the wellbore and displaces an equivalent amount of wellbore fluid to the surface through a second fluid conduit. In such an instance, the wellbore fluid includes a portion of the wellbore fluid previously contained in the wellbore before cement introduction as well as the amount of the introduced cement slurry.

As previously stated in this description, high density cements, which include cements with a density ranging from 140 pounds per cubic foot (pcf_ to 170 pcf are commonly used in wellbores because the high density cements are less porous than low density cements, which include cements with a density ranging from 65 pcf to 139 pcf, and, therefore, reduce the amount of undesirable components, such as undesirable hydrocarbons, that migrate from the geological formation into the tubular. However, internal pressure within the wellbore can cause tensile stress on the cement structure within the wellbore. Because the compressive strength of the cement is around ten times greater than the tensile strength of the cement, lesser tensile stresses placed on the cement component may be just as detrimental to the cement component as much greater compressive stresses. These tensile stresses can cause damage, such as cracks or fractures, to form in the cement structure. High density cements may be particularly prone to damage because the reduced porous structure of the high density cements, when compared to low density cements, may allow less flexibility in the cement structure. Once the cement structure is damaged, undesired component, such as undesired hydrocarbons, may migrate from the geological formation into the tubular.

This migration of components into the tubular can cause contamination of the wellbore product when the wellbore is in use, which required costly and time-consuming separations. Additionally, damage to the cement structure may allow components, such as undesired hydrocarbons, to migrate into the tubular after the wellbore is abandoned. These components can then move through the tubular and exit the wellbore, which may be detrimental to the environment.

In view of these previously discussed issues that can occur when the cement structure in the wellbore is damaged, the presently described flexible additives may be added to the cement structure. Without being bound to any particular theory, it is believed that the flexible additive forms a polymeric matrix within the cement structure that provides the cement structure with flexibility. This flexibility allows the cement structure to better withstand the tensile stresses caused by internal pressure in the wellbore.

Without being bound by theory, it is believed that the flexible additives presently described may have a beneficial effect with respect to one or more of the problems with cement damage, as described. As previously described in the present description, the flexible additive may comprise a hydrophilic polyolefin fiber, such as, in embodiments, 2,6-di-tert-butyl-p-cresol. It should be understood that while embodiments of flexible additives presently described include these components, other components may be included in a flexible additive for various functional reasons, and it is contemplated that additional components may be included in the flexible additives presently described.

As presently described, flexible additives according to embodiments comprise, consist, or consist essentially of one or more hydrophilic polyolefin fibers. In one or more embodiments, the flexible additive comprises, consists, or consists essentially of 2,6-di-tert-butyl-p-cresol.

According to one or more embodiments, the flexible additive may have a density from 1000 kilograms per cubic meter ($kg/m^3$) to 1700 $kg/m^3$, such as from 1050 $kg/m^3$ to 1700 $kg/m^3$, from 1100 $kg/m^3$ to 1700 $kg/m^3$, from 1150 $kg/m^3$ to 1700 $kg/m^3$, from 1200 $kg/m^3$ to 1700 $kg/m^3$, from 1250 $kg/m^3$ to 1700 $kg/m^3$, from 1300 $kg/m^3$ to 1700 $kg/m^3$, from 1350 $kg/m^3$ to 1700 $kg/m^3$, from 1400 $kg/m^3$ to 1700 $kg/m^3$, from 1450 $kg/m^3$ to 1700 $kg/m^3$, from 1500 $kg/m^3$ to 1700 $kg/m^3$, from 1550 $kg/m^3$ to 1700 $kg/m^3$, from 1600 $kg/m^3$ to 1700 $kg/m^3$, or from 1650 $kg/m^3$ to 1700 $kg/m^3$. In other embodiments, the density of the flexible additive is from 1000 $kg/m^3$ to 1650 $kg/m^3$, such as from 1000 $kg/m^3$ to 1600 $kg/m^3$, from 1000 $kg/m^3$ to 1550 $kg/m^3$, from 1000 $kg/m^3$ to 1500 $kg/m^3$, from 1000 $kg/m^3$ to 1450 $kg/m^3$, from 1000 $kg/m^3$ to 1400 $kg/m^3$, from 1000 $kg/m^3$ to 1350 $kg/m^3$, from 1300 $kg/m^3$ to 1700 $kg/m^3$, from 1000 $kg/m^3$ to 1250 $kg/m^3$, from 1000 $kg/m^3$ to 1200 $kg/m^3$, from 1000 $kg/m^3$ to 1150 $kg/m^3$, from 1000 $kg/m^3$ to 1100 $kg/m^3$, or from 1050 $kg/m^3$ to 1700 $kg/m^3$.

The specific gravity of the flexible additive according to one or more embodiments may be from 2.0 to 3.0, such as from 2.1 to 3.0, from 2.2 to 3.0, from 2.3 to 3.0, from 2.4 to 3.0. from 2.5 to 3.0, from 2.6 to 3.0, from 2.7 to 3.0, from 2.8 to 3.0, or from 2.9 to 3.0. In other embodiments, the specific gravity of the flexible additive is from 2.0 to 2.9, such as from 2.0 to 2.8, from 2.0 to 2.7, from 2.0 to 2.6, from 2.0 to 2.5, from 2.0 to 2.4, from 2.0 to 2.3, from 2.0 to 2.2, from 2.0 to 2.1. In still other embodiments, the specific gravity of the flexible additive is about 2.4, about 2.5, about 2.6, about 2.7, or about 2.8. Although not being bound to any particular theory, the density and specific gravity of the flexible additive presently described is believed to allow the flexible additive to move freely and be well-dispersed in the cement slurry so that the flexible additive may be uniformly present in the cement slurry and the cement structure once it is cured. A well-dispersed flexible additive allows the flexible additive to be present at or near any position in the cement structure, which allows for well-distributed polymeric matrix within the cured cement structure. Accordingly, the well-dispersed flexible additive may provide flexibility and durability to a cement structure such that the cement structure can withstand tensile stresses caused by internal pressure of the wellbore.

It should be understood that the presently described properties of the flexible additive may, in embodiments, not be uniformly present in the flexible additive. For instance, in embodiments where multiple hydrophilic polyolefin fibers are added to the flexible additive, each type of hydrophilic polyolefin fiber may have its own density and specific gravity. Accordingly, not every hydrophilic polyolefin fiber in the flexible additive will have the same properties. Although, in embodiments, each component of the flexible additive may have properties within the ranges presently described. In some embodiments, hydrophilic polyolefin fibers can include rubbers, polyacrylonitrile fibers, and mixtures thereof.

The flexible additive may additionally include one or more viscosifiers. The viscosifier induces rheological properties (that is, thickening) in the flexible additive composition that supports particle suspension and helps to prevent losses into the other fluids or the geological formation. The viscosifier can include biological polymers, clays, ethoxylated alcohols and polyether glycols. Biological polymers and their derivatives include polysaccharides, including xanthan gums, welan gums, guar gums, cellulose gums, corn, potato, wheat, maize, rice, cassava, and other food starches, succinoglycan, carrageenan, and scleroglucan and other intracellular, structural and extracellular polysaccharides. Biological polymers also include chemically modified derivatives such as carboxymethyl cellulose, polyanionic cellulose and hydroxyethyl cellulose (HEC) and forms of the polymers suspended in solvents. Clays and their derivatives include bentonite, sepiolite, attapulgite, and montmorillionite. Polyalklyene glycols include polyethylene glycols and polypropylene glycols, which are macromolecules with a series of internal ether linkages. Polyalklyene glycols are capable of dissolving in water and have a greater impact on viscosity with greater molecular weight.

The viscosifier can also include a viscosity thinner. A viscosity thinner reduces flow resistance and gel development by reducing viscosity of the flexible additive. Thinners comprising large molecular structures can also act as fluid loss additives. The functional groups of the viscosity thinners can act to emulsify oils and hydrocarbons present in the aqueous phase. Chemically modified viscosity thinners can attract solids and particles in the flexible additive and disperse such particles, the dispersion of particles preventing any increase in viscosity of the spacer fluid due to aggregation.

Polyphenolics, which include tannins, lignins, and humic acids, and chemically modified polyphenolics are useful viscosity thinners. Tannins and their chemically modified derivatives can either originate from plants or be synthetic. Examples of plant-originating tannins include tannins from pine, redwood, oak, and quebracho trees and bark; grapes and blueberries; and walnuts and chestnuts.

The flexible additive composition may also include one or more weighting agents. The weighting agent provides the flexible additive with the proper density profile. The proper weighing of the flexible additive composition relative to the cement slurry ensures that the flexible additive composition does not separate from the cement slurry. Weighting agents include sand, barite (barium sulfate), hematite, fly ash, silica sand, ilmenite, manganese oxide, manganese tetraoxide, zinc oxide, zirconium oxide, iron oxide and fly ash. According to one embodiment, the weighting agent for the flexible additive composition is barite.

A cement slurry may include water and a cement precursor, in addition to a presently described flexible additive. The cement slurry presently described may include silica sand with an average particle size from 80 to 120 microns, such as from 90 to 110 microns, or about 100 microns.

The cement slurry of the present description may include water, a cement precursor material, and the presently described flexible additive. The cement precursor material may be any suitable material which, when mixed with water, can be cured into a cement. The cement precursor material may be hydraulic or non-hydraulic. A hydraulic cement precursor material refers to a mixture of limestone, clay and gypsum burned together under extreme temperatures, such as temperatures up to 500° F. that may begin to harden instantly to within a few minutes while in contact with water. A non-hydraulic cement precursor material refers to a mixture of lime, gypsum, plasters and oxychloride. A non-hydraulic cement precursor may take longer to harden or may require drying conditions for proper strengthening, but often is more economically feasible. A hydraulic or non-hydraulic cement precursor material may be chosen based on the desired application of the cement slurry of the present description. While hydraulic cement may be more commonly utilized in drilling applications, it should be understood that other cements are contemplated. In some embodiments, the cement precursor material may be Portland cement precursor. Portland cement precursor is a hydraulic cement precursor (cement precursor material that not only hardens by reacting with water but also forms a water-resistant product) produced by pulverizing clinkers, which contain hydraulic calcium silicates and one or more of the forms of calcium sulphate as an inter ground addition. In embodiments, Portland cement was used, such as Portland cement Class G or Portland cement Class H. The Setting or thickening time, according to embodiments, is in a range from 30 minutes to 15 hours, such as from 5 hours to 10 hours. In embodiments, the curing temperature range is from 70 degrees Fahrenheit (° F.) to 500° F., such as from 200° F. to 300° F.

The cement precursor material may include one or more of calcium hydroxide, silicates, oxides, belite ($Ca_2SiO_5$), alite ($Ca_3SiO_4$), tricalcium aluminate ($Ca_3Al_2O_6$), tetracalcium aluminoferrite ($Ca_4Al_2Fe_2O_{10}$), brownmilleriate ($4CaO.Al_2O_3.Fe_2O_3$), gypsum ($CaSO_4.2H_2O$) sodium oxide, potassium oxide, limestone, lime (calcium oxide), hexavalent chromium, calcium alluminate, other similar compounds, and combinations of these. The cement precursor material may include Portland cement, siliceous fly ash, calcareous fly ash, slag cement, silica fume, any known cement precursor material or combinations of any of these. In one or more embodiments, the cement precursor comprises silica sand.

In some embodiments, the cement slurry may contain from 50% by weight of the cement (BWOC) to 90% BWOC of the cement precursor material based on the total weight of the cement slurry. For instance, the cement slurry may contain from 50% BWOC to 80% BWOC, from 50% BWOC to 70% BWOC, or from 50% BWOC to 60% BWOC. The cement slurry may contain from 55% BWOC to 90% BWOC, from 60% BWOC to 90% BWOC, from 70% BWOC to 90% BWOC, or from 75% BWOC to 90% BWOC of the cement precursor material.

Accordingly, in embodiments, the cement slurry may contain from 10% BWOC to 50% BWOC of the flexible additive based on the total weight of the cement slurry. For instance, the cement slurry may contain from 10% BWOC to 40% BWOC, from 10% BWOC to 30% BWOC, or from 10% BWOC to 20% BWOC. The cement slurry may contain from 15% BWOC to 50% BWOC, from 20% BWOC to 50% BWOC, from 30% BWOC to 50% BWOC, or from 40% BWOC to 50% BWOC of the flexible additive.

Water may be added to the cement precursor material to produce the slurry. The water may be distilled water, deionized water, brackish water, formation water, produced water, raw seawater, filtered seawater, or tap water. In some embodiments, the water may contain additives or contaminants. For instance, the water may include freshwater or seawater, natural or synthetic brine, or salt water. In some embodiments, salt or other organic compounds may be incorporated into the water to control certain properties of the water, and thus the cement slurry, such as density. Without being bound by any particular theory, increasing the saturation of water by increasing the salt concentration or the level of other organic compounds in the water may increase the density of the water, and thus, the cement slurry. Suitable salts may include, but are not limited to, alkali metal chlorides, hydroxides, or carboxylates. In some embodiments, suitable salts may include sodium, calcium, cesium, zinc, aluminum, magnesium, potassium, strontium, silicon, lithium, chlorides, bromides, carbonates, iodides, chlorates, bromates, formates, nitrates, sulfates, phosphates, oxides, fluorides, and combinations of these.

In some embodiments, the cement slurry may contain from 5% BWOC to 70% BWOC water based on the total weight of the cement slurry. In some embodiments, the cement slurry may contain from 5% BWOC to 50% BWOC, from 5% BWOC to 30% BWOC, 5% BWOC to 20% BWOC, from 5% BWOC to 10% BWOC, or from 10% BWOC to 70% BWOC, from 30% BWOC to 70% BWOC, or from 50% BWOC to 70% BWOC of water. The cement slurry may contain from 20% BWOC to 40% BWOC, or from 25% BWOC to 35% BWOC, such as 30% BWOC of water based on the total weight of the cement slurry.

The cement slurry presently described may also include an expansion additive. The expansion additive is used to achieve good bonding with the geological formation of the wellbore. As the cement dehydrates, its volume decreases, which causes a decreased bond between the cement and a casing or the cement and the geological formation. Expansion additives increase the volume of the cement and can improve the bonding as the cement dehydrates. At wellbore temperatures of 140° F. or greater, at least one of MgO, CaO, and mixtures thereof may be used as the expansion additive in the cement slurry. However, at temperatures less than 140° F., MgO does not expand quickly enough to provide adequate binding to the geological formation. Accordingly, at wellbore temperatures less than 140° F., crystalline $SiO_2$ may be used as the expansion additive because it expands more quickly than MgO. In one or more embodiments, D174 manufactured by Schlumberger may be used as a low-temperature expansion additive (such as, at temperatures less than 230° F.), Halliburton Micro bond L may be used as a low-temperature expansion additive (such as, at temperatures less than 230° F.), Halliburton Micro bond HT may be used as a high-temperature expansion additive (such as, at temperatures greater than 230° F.), and Schlumberger D 176 can be used as a high-temperature expansion additive (such as, at temperatures greater than 230° F.).

In some embodiments, the cement slurry may contain a weighting agent. Weighting agents may include, for example, magnesium tetraoxide ($Mn_3O_4$), hematite, calcium carbonate ($CaCO_3$), and barium sulfate ($BaSO_4$), and mixtures thereof. In one or more embodiments, the weighting agent is $Mn_3O_4$ because it can have a small particle size, spherical shape, and high specific gravity, which allows $Mn_3O_4$ to reduce solids loading and settling compared to other weighting agents.

In some embodiments, the cement slurry may contain from 0.1% BWOC to 50% BWOC of the one or more additional additives, as subsequently described, based on the total weight of the cement slurry. For instance, the cement slurry may contain from 0.1% BWOC to 8% BWOC of the one or more additional additives, from 0.1% BWOC to 5% BWOC of the one or more additives, or from 0.1% BWOC to 3% BWOC of the one or more additives. The cement slurry may contain from 1% BWOC to 10% BWOC of the one or more additives, from 1% BWOC to 8% BWOC, from 1% BWOC to 5% BWOC, or from 1% BWOC to 3% BWOC of the one or more additives. In some embodiments, the cement slurry may contain from 3% BWOC to 5% BWOC, from 3% BWOC to 8% BWOC, from 3% BWOC to 10% BWOC, or from 5% BWOC to 10% BWOC of the one or more additives.

In some embodiments, the one or more additional additives may include a dispersant containing one or more anionic groups. For instance, the dispersant may include synthetic sulfonated polymers, lignosulfonates with carboxylate groups, organic acids, hydroxylated sugars, other anionic groups, or combinations of any of these. Without being bound by any particular theory, in some embodiments, the anionic groups on the dispersant may be adsorbed on the surface of the cement particles to impart a negative charge to the cement slurry. The electrostatic repulsion of the negatively charged cement particles may allow the cement slurry to be dispersed and more fluid-like, improving flowability. This may allow for one or more of the following: turbulence at lesser pump rates; reduction of friction pressure when pumping; reduction of water content; and improvement of the performance of fluid loss additives.

In some embodiments, the one or more additional additives may alternatively or additionally include a fluid loss additive. In some embodiments, the cement fluid loss additive may include non-ionic cellulose derivatives. In some embodiments, the cement fluid loss additive may be hydroxyethylcellulose (HEC). In other embodiments, the fluid loss additive may be a non-ionic synthetic polymer (for example, polyvinyl alcohol or polyethyleneimine). In some embodiments, the fluid loss additive may be an anionic synthetic polymer, such as 2-acrylamido-2-methylpropane sulfonic acid (AMPS) or AMPS-copolymers, including lattices of AMPS-copolymers. In some embodiments, the fluid loss additive may include bentonite, which may additionally viscosify the cement slurry and may, in some embodiments, cause retardation effects. Without being bound by any particular theory, the surfactant may reduce the surface tension of the aqueous phase of the cement slurry, thus reducing the fluid lost by the slurry. Additionally, the carboxylic acid may further reduce the fluid loss of the cement slurry by plugging the pores of the cement filter cake, minimizing space for the water or other fluids to escape from the cement.

In some embodiments, the fluid loss additive may contain a carboxylic fatty acid having from 16 to 18 carbon atoms, which may be used in combination with the surfactant to reduce fluid loss in the cement slurry. The carboxylic fatty acid includes any acids having formula ROOH in which R is a saturated or unsaturated, linear, or branched hydrocarbyl group having from 16 to 18 carbons, such as a hydrocarbyl group having 16 carbons, 17 carbons, or 18 carbons. Examples of suitable carboxylic fatty acids include palmitic acid, palmitoleic acid, vaccenic acid, oleic acid, elaidic acid, linoleic acid, α-linolenic acid, γ-linolenic acid, stearidonic acid, and combinations thereof. The surfactant may be in accordance with any of the embodiments previously described. In some specific embodiments, the fluid loss additive may contain a combination of an ethylene oxide condensate of branched isotridecyl alcohol with a fatty acid having from 16 to 18 carbon atoms in the hydrocarbyl group.

Following introduction of the cement slurry into the wellbore, the cement slurry may form cement through curing. As used throughout the description, "curing" refers to providing adequate moisture, temperature and time to allow the concrete to achieve the desired properties (such as hardness) for its intended use through one or more reactions between the water and the cement precursor material. Curing may be a passive step where no physical action is needed (such as cement that cures in ambient conditions when untouched). In contrast, "drying" refers to merely allowing the concrete to achieve a moisture condition appropriate for its intended use, which may only involve physical state changes, as opposed to chemical reactions. In some embodiments, curing the cement slurry may refer to passively allowing time to pass under suitable conditions upon which the cement slurry may harden or cure through allowing one or more reactions between the water and the cement precursor material. Suitable conditions may be any time, temperature, pressure, humidity, and other appropriate conditions known in the cement industry to cure a cement composition. In some embodiments, suitable curing conditions may be ambient conditions. Curing may also involve actively hardening or curing the cement slurry by, for instance, introducing a curing agent to the cement slurry, providing heat or air to the cement slurry, manipulating the environmental conditions of the cement slurry to facilitate reactions between the water and the cement precursor, a combination of these, or other such means.

In some embodiments, curing may occur at a relative humidity of greater than or equal to 80% in the cement slurry and a temperature of greater than or equal to 50° F. for a time period of from 1 to 14 days. Curing may occur at a relative humidity of from 80% to 100%, such as from 85% to 100%, or 90% to 100%, or from 95% to 100% relative humidity in the cement slurry. The cement slurry may be cured at temperatures of greater than or equal to 50° F., such as greater than or equal to 75° F., greater than or equal to 80° F., greater than or equal to 100° F., or greater than or equal to 120° F. The cement slurry may be cured at temperatures of from 50° F. to 250° F., or from 50° F. to 200° F., or from 50° F. to 150° F., or from 50° F. to 120° F. The cement slurry may be cured for from 1 day to 14 days, such as from 3 to 14 days, or from 5 to 14 days, or from 7 to 14 days, or from 1 to 3 days, or from 3 to 7 days.

Once the cement slurry is cured, the cured cement constitutes a cement structure within the wellbore. The cement structure will have various properties that indicate the physical strength and flexibility of the cement structure. For instance, Young's modulus measures the ratio of the stress (force per unit area) along an axis to the strain (ratio of deformation over initial length) along that axis. Thus, Young's modulus can be used to show the elasticity or stiffness of the cement structure within the wellbore and gives insight into the tensile strength of the cement structure. Poisson's ratio is a measure of transverse strain to axial strain, and measures the deformation capacity of the cement structure. The greater the deformation capacity (that is, the greater Poisson's ratio) the less likely the cement structure will be damaged as temperature and pressure changes within the wellbore. The Young's modulus and Poisson's ratio were measure 10 days after curing the cement structure, 20 days after curing the cement structure, and 30 days after curing the cement structure.

In one or more embodiments, the static Young's modulus of the cement structure 10 days after curing is from $0.90 \times 10^6$ pounds per square inch (psi) to $1.20 \times 10^6$ psi, such as from $0.95 \times 10^6$ psi to $1.20 \times 10^6$ psi, from $1.00 \times 10^6$ psi to $1.20 \times 10^6$ psi, from $1.05 \times 10^6$ psi to $1.20 \times 10^6$ psi, from $1.10 \times 10^6$ psi to $1.20 \times 10^6$ psi, or from $1.15 \times 10^6$ psi to $1.20 \times 10^6$ psi. In other embodiments, the static Young's modulus of the cement structure 10 days after curing is from $0.90 \times 10^6$ psi to $1.15 \times 10^6$ psi, such as from $0.90 \times 10^6$ psi to $1.10 \times 10^6$ psi, from $0.90 \times 10^6$ psi to $1.05 \times 10^6$ psi, from $0.90 \times 10^6$ psi to $1.00 \times 10^6$ psi, or from $0.90 \times 10^6$ psi to $0.95 \times 10^6$ psi. In one or more embodiments, the static Young's modulus of the cement structure 20 days after curing is from $0.90 \times 10^6$ psi to $1.20 \times 10^6$ psi, such as from $0.95 \times 10^6$ psi to $1.20 \times 10^6$ psi, from $1.00 \times 10^6$ psi to $1.20 \times 10^6$ psi, from $1.05 \times 10^6$ psi to $1.20 \times 10^6$ psi, from $1.10 \times 10^6$ psi to $1.20 \times 10^6$ psi, or from $1.15 \times 10^6$ psi to $1.20 \times 10^6$ psi. In other embodiments, the static Young's modulus of the cement structure 20 days after curing is from $0.90 \times 10^6$ psi to $1.15 \times 10^6$ psi, such as from $0.90 \times 10^6$ psi to $1.10 \times 10^6$ psi, from $0.90 \times 10^6$ psi to $1.05 \times 10^6$ psi, from $0.90 \times 10^6$ psi to $1.00 \times 10^6$ psi, or from $0.90 \times 10^6$ psi to $0.95 \times 10^6$ psi. In one or more embodiments, the static Young's modulus of the cement structure 30 days after curing is from $0.90 \times 10^6$ psi to $1.20 \times 10^6$ psi such as from $0.95 \times 10^6$ psi to $1.20 \times 10^6$ psi, from $1.00 \times 10^6$ psi to $1.20 \times 10^6$ psi, from $1.05 \times 10^6$ psi to $1.20 \times 10^6$ psi, from $1.10 \times 10^6$ psi to $1.20 \times 10^6$ psi, or from $1.15 \times 10^6$ psi to $1.20 \times 10^6$ psi. In other embodiments, the static Young's modulus of the cement structure 30 days after curing is from $0.90 \times 10^6$ psi to $1.15 \times 10^6$ psi, such as from $0.90 \times 10^6$ psi to $1.10 \times 10^6$ psi, from $0.90 \times 10^6$ psi to $1.05 \times 10^6$ psi, from $0.90 \times 10^6$ psi to $1.00 \times 10^6$ psi, or from $0.90 \times 10^6$ psi to $0.95 \times 10^6$ psi.

In one or more embodiments, the static Poisson's ratio of the cement structure 10 days after curing is from 0.120 psi to 0.140 psi, such as from 0.125 psi to 0.140 psi, from 0.130 psi to 0.140 psi, or from 0.135 psi to 0.140 psi. In other embodiments, the static Poisson's ratio of the cement structure 10 days after curing is from 0.120 psi to 0.135 psi, from 0.120 psi to 0.130 psi, or from 0.120 psi to 0.125 psi. In one or more embodiments, the static Poisson's ratio of the cement structure 20 days after curing is from 0.110 psi to 0.130 psi, such as from 0.115 psi to 0.130 psi, from 0.120 psi to 0.130 psi, or from 0.125 psi to 0.130 psi. In other embodiments, the static Poisson's ratio of the cement structure 20 days after curing is from 0.110 psi to 0.125 psi, from 0.110 psi to 0.120 psi, or from 0.110 psi to 0.115 psi. In one or more embodiments, the static Poisson's ratio of the cement structure 30 days after curing is from 0.190 psi to 0.210 psi, from 0.195 psi to 0.210 psi, from 0.200 psi to 0.210 psi, or from 0.205 psi to 0.210 psi. In other embodiments, the static Poisson's ratio of the cement structure 30 days after curing is from 0.190 psi to 0.205 psi, from 0.190 psi to 0.200 psi, or from 0.190 psi to 0.195 psi.

The cement structure may, in embodiments, have a density from 1.80 grams per cubic centimeter (g/cc) to 2.20 g/cc, such as from 1.85 g/cc to 2.15 g/cc from 1.90 g/cc to 2.10 g/cc, from 1.95 g/cc to 2.05 g/cc, or about 2.00 g/cc. the cement structure may include pores that allow undesirable components, such as undesirable hydrocarbons, to migrate from the geological formation into the tubular through the cement structure. However, if the density of the cement structure exceeds 170 pounds per cubic foot (pcf), the cement structure may not have enough elasticity to survive exposure to tensile stresses caused by internal pressures in the wellbore. As presently described, flexible additives according to embodiments may be used in a wide array of cements have many densities.

A first aspect includes, a cement slurry comprising: 50% to 90% BWOC of a cement precursor material based on a total weight of the cement slurry; and from 10% to 50% BWOC of a flexible additive based on the total weight of the cement slurry, where the flexible additive comprises hydrophilic polyolefin fibers or 2,6-di-tert-butyl-p-cresol.

A second aspect includes the cement slurry of the first aspect, where the flexible additive comprises 2,6-di-tert-butyl-p-cresol.

A third aspect includes the cement slurry of any one of the first and second aspects, where the flexible additive consists essentially of 2,6-di-tert-butyl-p-cresol.

A fourth aspects includes the cement slurry of the first aspect, where the flexible additive comprises hydrophilic polyolefin fibers selected from the group consisting of rubbers, polyacrylonitrile fibers, and mixtures thereof.

A fifth aspect includes the cement slurry of any one of the first to fourth aspects, where the flexible additive has a density from 1000 kg/m$^3$ to 1700 kg/m$^3$.

A sixth aspect includes the cement slurry of any one of the first to fifth aspects, where the flexible additive has a specific gravity from 2.0 to 3.0.

A seventh aspect includes the cement slurry of any one of the first to sixth aspects, where the cement slurry comprises from 10% to 30% BWOC of the flexible additive based on the total weight of the cement slurry.

An eighth aspect includes a wellbore cementing system comprising: a tubular positioned in a wellbore such that an annulus is formed between a geological formation and the tubular; and a cement structure positioned in at least a portion of the annulus, where the cement structure comprises from 10% to 50% BWOC of a flexible additive, and where the flexible additive comprises hydrophilic polyolefin fibers or 2,6-di-tert-butyl-p-cresol.

A ninth aspect includes the wellbore cementing system of the eighth aspect, where the flexible additive comprises 2,6-di-tert-butyl-p-cresol.

A tenth aspect includes the wellbore cementing system of any one of the eighth and ninth aspects, where the flexible additive consists essentially of 2,6-di-tert-butyl-p-cresol.

An eleventh aspect includes the wellbore cementing system of the eighth aspect, where the flexible additive comprises hydrophilic polyolefin fibers selected from the group consisting of rubbers, polyacrylonitrile fibers, and mixtures thereof.

A twelfth aspect includes the wellbore cementing system of any one of the eighth to eleventh aspects, where the flexible additive has a density from 1000 kg/m$^3$ to 1700 kg/m$^3$.

A thirteenth aspect includes the wellbore cementing system of any one of the eighth to twelfth aspects, where the flexible additive has a specific gravity from 2.0 to 3.0.

A fourteenth aspect includes the wellbore cementing system of any one of the eighth to thirteenth aspects, where the cement structure comprises from 10% to 30% BWOC of the flexible additive based on a total weight of the cement structure.

A fifteenth aspect includes the wellbore cementing system of any one of the eighth to fourteenth aspects, where the cement structure has a Young's modulus 10 days after curing from $0.90 \times 10^6$ psi to $1.20 \times 10^6$ psi.

A sixteenth aspect includes the wellbore cementing system of any one of the eighth to fifteenth aspects, where the cement structure has a Young's modulus 20 days after curing from $0.90 \times 10^6$ psi to $1.20 \times 10^6$ psi.

A seventeenth aspect includes the wellbore cementing system of any one of the eighth to sixteenth aspects, where the cement structure has a Young's modulus 30 days after curing from $0.90 \times 10^6$ psi to $1.20 \times 10^6$ psi.

An eighteenth aspect includes the wellbore cementing system of any one of the eighth to seventeenth aspects, where the cement structure has a Poisson's ratio 10 days after curing from 0.120 psi to 0.140 psi.

A nineteenth aspect includes the wellbore cementing system of any one of the eighth to eighteenth aspects, where the cement structure has a Poisson's ratio 20 days after curing from 0.110 psi to 0.130 psi.

A twentieth aspect includes the wellbore cementing system of any one of the eighth to nineteenth aspects, where the cement structure has a Poisson's ratio 30 days after curing from 0.190 psi to 0.210 psi.

EXAMPLES

The following example illustrates one or more features of the present description. It should be understood that these examples are not intended to limit the scope of the description or the appended claims in any manner.

A cement slurry was tested for rheology, thickening time, fluid loss, free water, sedimentation, expansion performance, and mechanical properties in order to evaluate the performance of cement slurry. The cement slurry included silica sand with an average particle size of 100 microns, crystalline silica expansion additives, and a 2,6-di-tert-butyl-p-cresol flexible additive. Two sizes of crystalline silica were used; Schlumberger micro fine silica (D178) and Schlumberger coarse silica (D030).

The cement slurry formulation was prepared in the lab using the standard American Petroleum Institute (API) blender. The maximum speed used during slurry preparation was 12,000 rotations per minute (rpm). The slurry was mixed in the blender for 15 seconds at 4,000 rpm and 35 seconds at 12,000 rpm. The slurry was then conditioned in the atmospheric consistometer before obtaining the rheological measurements. A Fann viscometer (Model-35) was utilized to measure the slurry apparent viscosity.

The prepared slurry was then poured into API standard High Pressure/High Temperature (HP/HT) consistometer slurry cup for a thickening time test, which is important to evaluate the pumpability of the cement slurry.

As in API Recommended testing 10-B2, a free water test was used to measure water separation by using 250 milliliter (ml) graduated cylinder in the cement slurry for 2 hours. Settling was measured by comparing densities of different sections of the cement column cured. The cylindrical shaped cell, used to cure the cement formula for settling test, had a diameter of 1.4" and length of 12". Sections of 2" long were taken from different parts of the cement column sample. The cement slurry was cured at 8000 psi and 300° F. for at least 3 days.

To measure expansion, an annular expansion ring test was used to measure linear expansion under condition of free access to water. Free access to water means an open system. An annular expansion mold was used to simulate the annulus of the well. The cement slurry was poured into the annular space in the mold and then the mold was placed into water bath or a pressurized curing chamber. Water was in contact with the slurry during the entire curing process as in API Recommended testing 10-B2. The diameter increased if the cement expanded.

A composition and properties of the cement slurry is provided in Table 1 and properties of the cement slurry are provided in Tables 2 and 3. In Table 2, the rheology of the cement slurry was measured using a standard viscometer. Ramp up in Table 2 indicates increasing rpm to 3, 6, 100, 200, and 300. Ramp down in Table 2 indicates decreasing rpm from 300 to 200, 100, 6, and 3. In Table 3 the thickening time of the slurry is measured by pouring the slurry into a cylinder with 0 degree inclination (a vertical cylinder) and heating to 80° F. for several hours. The solid sedimentation at the bottom section of the cylinder is observed. No sedimentation means that cement will have good quality at both the top and the bottom of the cement structure. The API fluid loss is a test that measures the volume of filtrate of the cement slurry at high temperature and pressure. As used in this example, high temperature is in a range from 180° F. to 500° F., and high pressure is in a range from 5,000 psi to 20,000 psi. In Table 3, the "BC" is the Bearden unit of consistency, and an acceptable fluid level is 0 ml/250 ml at atmospheric conditions. In this example, the components listed in Table 1 were all manufactured by Schlumberger, and the Schlumberger material number is listed in Table 1.

TABLE 1

| Cement Slurry: | | |
|---|---|---|
| Component | Concentration | Unit of Measure |
| Fresh water | 5.267 | gps |
| Flexible Additive (D196) | 20.300 | % BWOC |
| Silica (D030) | 10.200 | % BWOC |
| Silica (D178) | 30.900 | % BWOC |
| Weighting Agent (D157) | 56.200 | % BWOC |
| High Temp. Expansive Agent (D176) | 3.000 | % BWOC |
| Antifoam (D175) | 0.062 | gps |

TABLE 1-continued

Cement Slurry:

| Component | Concentration | Unit of Measure |
|---|---|---|
| Dispersant (D065) | 0.660 | % BWOC |
| Fluid Loss (D167) | 0.330 | % BWOC |
| Retarder (D800) | 0.700 | % BWOC |
| GASBLOK (D600G) | 1.452 | gps |
| GASBLOK stabilizer (D135) | 0.207 | gps |

TABLE 2

Rheology of the Cement Slurry:
Rheology at 81 F.

| RPM | Ramp up (measurement) | Ramp down (measurement) | Average |
|---|---|---|---|
| 300 | 128 | 128 | 128 |
| 200 | 89 | 95 | 92 |
| 100 | 53 | 57 | 55 |
| 60 | 37 | 40 | 39 |
| 30 | 25 | 28 | 26 |
| 6 | 15 | 14 | 15 |
| 3 | 13 | 13 | 13 |

TABLE 3

Properties of Cement Slurry:

Thickening time

| Consistency | Time |
|---|---|
| 67 Bc | 7:35 hrs |

Free Fluid 0 ml/250 ml in 2 hrs
80 F., 0 deg inclination
No sedimentation

Fluid loss

API fluid loss 76 ml
14 min, 185 F., and 1000 psi

Single stage triaxial tests were performed on 13 dry cement core plugs with lengths ranging between 2.997 and 3.020 inches and having a diameter between 1.490 and 1.510 inches to measure static and dynamic properties through ultrasonic and shear velocities. These properties were determined at a confining pressure of 1 megapascals (MPa) (1 MPa=145.038 psi) and included the Young's modulus, the Poisson's Ratio, the Peak Strength.

During each test performed, a series of ultrasonic measurements and dynamic moduli were computed. The final dynamic moduli of a plug were taken as the average of the moduli computed at each ultrasonic velocity measurement.

Sample Preparation included the following steps: (1) cement core plug formulation was selected and drilled; (2) surfaces of the parallel end faces were grinded until they became flat to within 0.001 inches; and (3) the plug was jacketed and positioned so that two end caps equipped with velocity transducers could be placed on the ends of the sample while a coupling medium was set between the plug flat surfaces and the transducer.

After completing the sample preparation as per the procedure in the preceding paragraph, the plug was equipped and loaded onto the testing frame as follows: (a) the jacket was clamped to the transducers from both ends to allow for the hydrostatic confining pressure around the sample to be applied; (b) radial and axial limited variable differential transformers (LVTD) were positioned around and along the sample to measure radial and axial displacements respectively; and (c) confining pressure was applied hydrostatically around the sample. The confining pressures were selected to simulate the stress condition in the vicinity of the wellbore.

For this example single stage triaxial tests at low confining pressures were conducted. The dynamic elastic properties were determined simultaneously with the static properties using ultrasonic measurements. The static properties are required for many petroleum engineering applications; however, dynamic data are often collected in the field and therefore the necessary calibration must be obtained to design specific treatments related to wellbore stability, hydraulic fracturing, and sand control.

To perform dynamic measurements (ultrasonic velocity measurements) the end caps of the core sample were equipped with ultrasonic transducers and receivers which can generate and detect, respectively, both compressional and shear waves. One transducer was a transmitter which was excited to induce an ultrasonic wave at a frequency of 700 kilohertz (kHz) and the other one was a receiver. In this example the velocities of these waves were used to compute the dynamic Young's modulus and Poisson's ratio.

Mechanical Properties Simulation

Young's modulus E characterizes the material's longitudinal deformation under uniaxial loading, such as along an axis when opposing forces are applied along that axis. Transverse deformation is quantified with the Poisson's ratio υ, which is the ratio between transverse and axial deformation. A Poisson's ratio equal to 0.5 means the material is incompressible. Conventional cements have a Poisson's ratio of approximately 0.15.

Results of the mechanical properties are shown in Table 4.

TABLE 4

Cement slurry (105 pcf) mechanical test results measured according to ASTM D2850 and D4767 Standard Test Methods.

| Sample | Sat. bulk density (g/cc) | Confining pressure (psi) | Static Young's modulus (psi) | Dynamic Young's modulus (psi) | Static Poisson's ration | Dynamic Poisson's ration | Peak strength | Remarks |
|---|---|---|---|---|---|---|---|---|
| Comp. Ex. 1 | 1.99 | 447.5 | $2.52 \times 10^6$ | $2.64 \times 10^6$ | 0.168 | 0.308 | 12312 | 10 days conventional cement |
| 1 | 1.99 | 168 | $1.09 \times 10^6$ | $3.10 \times 10^6$ | 0.129 | 0.305 | 5203 | 10 days durable cement |

TABLE 4-continued

Cement slurry (105 pcf) mechanical test results measured according to ASTM D2850 and D4767 Standard Test Methods.

| Sample | Sat. bulk density (g/cc) | Confining pressure (psi) | Static Young's modulus (psi) | Dynamic Young's modulus (psi) | Static Poisson's ration | Dynamic Poisson's ration | Peak strength | Remarks |
|---|---|---|---|---|---|---|---|---|
| 2 | 1.99 | 472 | $1.10 \times 10^6$ | $1.65 \times 10^6$ | 0.118 | 0.32 | 4415 | 20 days durable cement |
| 3 | 1.99 | 477 | $1.08 \times 10^6$ | $1.89 \times 10^6$ | 0.205 | 0.298 | 4924 | 30 days durable cement |

Having described the subject matter of the present description in detail and by reference to specific embodiments, it is noted that the various details described in this description should not be taken to imply that these details relate to elements that are essential components of the various embodiments described in this description, even in cases where a particular element is illustrated in each of the drawings that accompany the present description. Rather, the claims infra should be taken as the sole representation of the breadth of the present description and the corresponding scope of the various embodiments described in this description. Further, it should be apparent to those skilled in the art that various modifications and variations can be made to the described embodiments without departing from the spirit and scope of the claimed subject matter. Thus it is intended that the specification cover the modifications and variations of the various described embodiments provided such modification and variations come within the scope of the claims recited infra and their equivalents.

It should be understood that any two quantitative values assigned to a property may constitute a range of that property, and all combinations of ranges formed from all stated quantitative values of a given property are contemplated in this description. It should be appreciated that compositional ranges of a chemical constituent in a composition or formulation should be appreciated as containing, in some embodiments, a mixture of isomers of that constituent. It should be appreciated that the examples supply compositional ranges for various compositions, and that the total amount of isomers of a particular chemical composition can constitute a range.

As used in the Specification and appended Claims, the singular forms "a", "an", and "the" include plural references unless the context clearly indicates otherwise. The verb "comprises" and its conjugated forms should be interpreted as referring to elements, components or steps in a non-exclusive manner. The referenced elements, components or steps may be present, utilized or combined with other elements, components or steps not expressly referenced.

Where a range of values is provided in the Specification or in the appended Claims, it is understood that the interval encompasses each intervening value between the upper limit and the lower limit as well as the upper limit and the lower limit. The invention encompasses and bounds smaller ranges of the interval subject to any specific exclusion provided. As used herein, the word "about" followed by a number includes the stated number plus or minus two significant digits.

What is claimed is:

1. A wellbore cementing system comprising:
   a tubular positioned in a wellbore such that an annulus is formed between a geological formation and the tubular; and
   a cement structure positioned in at least a portion of the annulus, where
   the cement structure comprises from 10% to 50% by weight of cement of a flexible additive based on the total weight of the cement structure, and
   where the flexible additive comprises 2,6-di-tert-butyl-p-cresol.

2. The wellbore cementing system of claim 1, where the flexible additive consists essentially of 2,6-di-tert-butyl-p-cresol.

3. The wellbore cementing system of claim 1, where the flexible additive has a density from 1000 kg/m$^3$ to 1700 kg/m$^3$.

4. The wellbore cementing system of claim 1, where the flexible additive has a specific gravity from 2.0 to 3.0.

5. The wellbore cementing system of claim 1, where the cement structure comprises from 10% to 30% by weight of cement of the flexible additive based on the total weight of the cement structure.

6. The wellbore cementing system of claim 1, where the cement structure has a Young's modulus 10 days after curing from $0.90 \times 10^6$ psi to $1.20 \times 10^6$ psi.

7. The wellbore cementing system of claim 1, where the cement structure has a Young's modulus 20 days after curing from $0.90 \times 10^6$ psi to $1.20 \times 10^6$ psi.

8. The wellbore cementing system of claim 1, where the cement structure has a Young's modulus 30 days after curing from $0.90 \times 10^6$ psi to $1.20 \times 10^6$ psi.

9. The wellbore cementing system of claim 1, where the cement structure has a Poisson's ratio 10 days after curing from 0.120 psi to 0.140 psi.

10. The wellbore cementing system of claim 1, where the cement structure has a Poisson's ratio 20 days after curing from 0.110 psi to 0.130 psi.

11. The wellbore cementing system of claim 1, where the cement structure has a Poisson's ratio 30 days after curing from 0.190 psi to 0.210 psi.

* * * * *